US00PP08895P

United States Patent [19]

Denis

[11] Patent Number: Plant 8,895

[45] Date of Patent: Sep. 13, 1994

[54] FICUS ELASTICA PLANT NAMED SYLVIE

[75] Inventor: Rene G. M. A. Denis, Destelbergen, Belgium

[73] Assignee: Denis-Plants B.V.B.A., Beervelde, Belgium

[21] Appl. No.: 120,444

[22] Filed: Sep. 14, 1993

[51] Int. Cl.[5] ..... A01H 5/00

[52] U.S. Cl. ..... Plt./88.9

[58] Field of Search ..... Plt. 88.9

[56] References Cited

PUBLICATIONS

Huxley, A., et al., "*Ficus*" *The New Royal Horticultural Society Dictionary of Gardening,* 2, D–K, 1992, The Stocton Press, pp. 294–305.

Graf, A. B., "Moraceae: *Ficus elastica* 'Doescheri'etc.", *Tropica* Roehrs Co., 1978, pp. 650–652; 1001–1002.

Graf, A. B., "Moraceae: *Ficus*" *Exotica* Roehrs Co., 1963, pp. 1157; 1613–1615.

Bailey, L. H., et al., "*Ficus*" *Hortus Third* 1976 Macmillan Pub. Co., Inc., N.Y. 1976 pp. 477–479.

*Primary Examiner*—James R. Feyrer

*Attorney, Agent, or Firm*—Foley & Lardner

[57] ABSTRACT

A new cultivar of *Ficus elastica* plant Sylvie, particularly characterized by its green to dark green marking along the midribs of the leaves surrounded by a white-yellow to white color to the leaf margins. In new leaves the surrounding color is white-yellow, with such color turning to white as the leaf matures. The surrounding color comprises about 50% of the leaf surface. In between the white surrounding and the dark green irregular marking along the midrib is a color combination of lighter green to grey.

2 Drawing Sheets

The present invention comprisea a new and distinct cultivar of *Ficus elastica,* known by the cultivar name Sylvie.

Sylvie is a mutation discovered by the inventor Rene G. M. A. Denis in greenhouses in Lochristi-Beervelde, Belgium in 1989. The new cultivar was discovered growing among plants of the parent cultivar *Ficus elastica* 'Belga' (hereafter Belga), and was recognized due to its special leaf color. The parent cultivar Belga was propagated in Belgium for many decades, and is understood by the inventor to be the variety disclosed in U.S. Plant Pat. No. 2,220.

The first act of asexual reproduction of Sylvie was accomplished by tissue culture later in 1989 in a laboratory in Lochristi-Beervelde, Belgium by applicant. Horticultural examination of Sylvie has demonstrated that the combination of characteristics as herein disclosed for the new cultivar are firmly fixed and are retained through successive generations of asexual reproduction, which can be performed by cuttings in addition to tissue culture.

Sylvie has not been observed under all possible environmental conditions. The phenotype may vary somewhat with variations in environment such as temperature, light intensity, and daylength, without, however, any variation in genotype. The following observations, measurements and comparisons describe plants grown in Lochristi-Beervelde, Belgium, under greenhouse conditions which closely approximate those generally used in horticultural practice.

The following traits have been repeatedly observed to be characteristics which in combination distinguish Sylvie from other varieties of *Ficus elastica* with which the inventor is familiar.

1. The leaf color of 'Sylvie' is white to light yellow, with dark green variegation of varying dimension from the midrib to both sides. The leaf color can be compared with the parent 'Belga', which is also white, but the amount of white color in Sylvie is much larger compared to the green, which results in a totally different plant. 'Sylvie' also differs in this respect from other varieties of *Ficus elastica* with which applicant is familiar.

2. New leaves have more white-yellow surroundings, which turn to white for older leaves. Older leaves which are not exposed totally to light, or plants which are cultivated too dark, occasionally have brown spots on the white surrounding have of the leaves. This can only be avoided by giving the plant enough light during culture time and also afterwards.

3. Sylvie has a green to dark green irregular marking along the midrib, which is similar in color to other known *Ficus elastica* cultivars having variegated leaves. However where this marking comprises 90 to 95% of the leaf surface of the parent 'Belga', the marking of 'Sylvie' is restricted to approximately 50% of the leaf surface. Thus, where the white color of Belga is restricted to marginal variegation of the leaf, the white color of 'Sylvie' comprises a dominating color of the leaf. Such dominance of the surrounding color of marginal variegation is comparable to *Ficus benjamina* Starlight, but the color is distinctly different.

4. In between the white surrounding and the dark green irregular marking along the mibrib, there is a color combination of lighter green to grey, which is divided just near or in between the darker green.

5. The combination of 50% white and 50% darker green only occurs 4 to 6 leaves after multiplication. First leaves after cutting are more green and less white.

6. The color of the midrib is red to red-pink, and can be distinguished clearly from the dark green marking in the middle of the leaves.

All color references are measured against The Royal Horticultural Society Color Chart. Color may vary somewhat depending on horticultural practices such as light level, temperature, and fertilization rate, among others.

The accompanying color photographic drawings illustrate a typical specimen plant of Sylvie, with photographic color depicting true colors to the extent possible with reproductions of this type. The photo on sheet 1 shows a plant with several leaves which possess at different stages the unique variegation of the new cultivar. The photo at the top of sheet 2 illustrates the white-yellow surrounding color of young leaves. The photo at the bottom of sheet 2 shows three different nature leaves showing various degrees white to gray/green variegation.

Origin: Mutation discovered among tissue culture of *Ficus elastica* Belga.

Classification: *Ficus elastica* c.v. Sylvie.

Propagation: By cuttings or tissue culture. By taking cuttings from cuttings, plants turn more and more to white after several generations, which results in a slower growing plant. This is avoided by using tissue cultured plants as mother plants. By regularly changing mother stock and by limiting the quantity cut from one mother plant, uniformity of propagative plants is established, and plants continue growing well.

Plant: The plant has the usual *Ficus elastica* shape. The main stem is vertically upright, with the branches being at an angle of 45° to 60°. Ramification is rare, except with tissue cultured plants. When propagated by cuttings, ramification occurs only on older plants whose height is 80 to 100 cm, or more. Young parts of the stem are light green in color and start to cork quickly from the bases of the petiole. Corking then continues from the lenticells with a design of vertical ribbons. Lenticells are spread, vertical to oval, and light green with a red-brown point.

Growth: The general appearance and growing habit of Sylvie corresponds to either varieties of the species. However, due to larger areas of white in the leaves and therefore less chlorophyll, Sylvie is a slower grower than Belga or *Ficus elastica* Tricolor disclosed in U.S Plant Pat. No. 4,069 (FIGS. 5A and 5B).

Leaves:

*Shape.*—Elliptic to acuminate with a rather long pointed tip.

*Form.*—Elliptic to acuminate with a rather long pointed top, thick and leathery. Sylvie has a more round leaf, compared to the generally oval shaped leaves of Belga and Tricolor.

*Size.*—18 to 24 cm long, 9 to 15 cm wide.

*Margin.*—Smooth.

*Aspect.*—The surface of the leaf is slightly undulating or wavy.

*Texture.*—Slightly glossy, luxuriant.

*Petiole.*—About 2 to 3.5 cm long.

*Veins.*—A rather thick midrib and normal side veins extending from midrib to margin. The midrib on new leaves is light purple to pink in color, later changing to light grey-green on the underside and ivory white on the upperside.

*Variegation.*—Among the midrib are dark green irregular markings that occupy 50% of the leaf surface.

*Color.*—Upper surface: The background of older or mature leaves is white-grey 156 B. On the leaf there is a dark green 139 A marking, which changes with clear surroundings from dark grey green 189 A to light grey 190 A to 190 B. The younger leaves have the same 139 A marking, which also changes from 189 A to light grey 190 A-190 B, but the background is more white-yellow, 160 C. Lower surface: The lower surface has the same white-yellow 160 C color as on the upper surface. The dark marking is not present on the lower surface, but can be seen through from the upper surface. Upper surface midrib: The upper surface midrib is red 62 B to red-pink 73 B. Lower surface midrib: The lower surface midrib is the same red 62 B to red-pink 73 B. Petiole: The color of the petiole is red 62 B to red-pink 73 B.

Inflorescence: Insignificant.

Reproductive organs: Normal.

Roots: Good rooting system.

I claim:

1. A new and distinct cultivar of *Ficus elastica* named Sylvie, as illustrated and described.

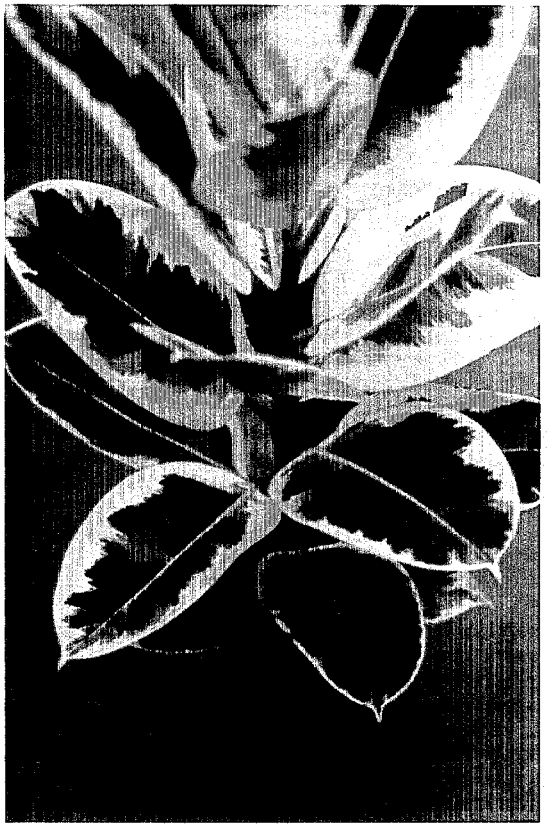

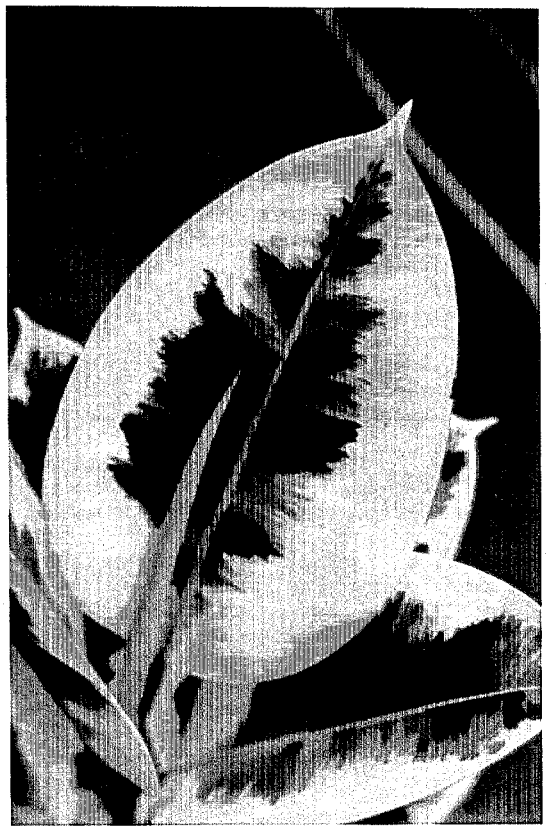
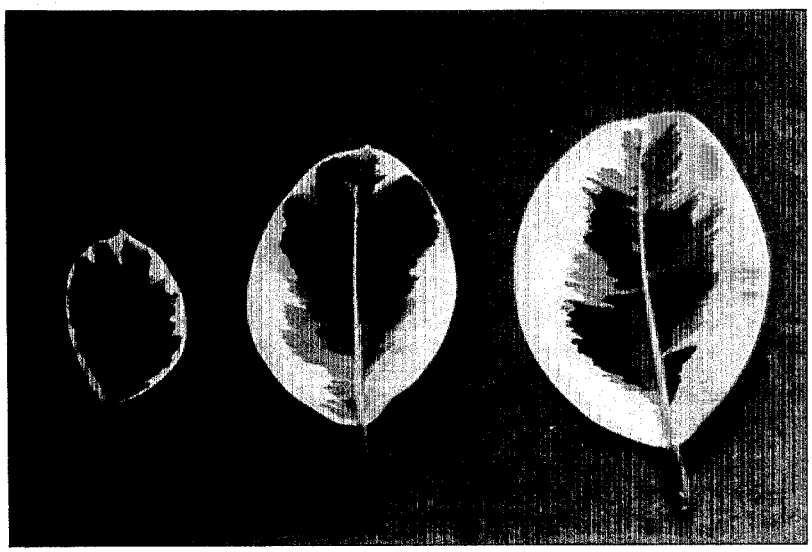

* * * * *